United States Patent [19]

Hertzsch et al.

[11] Patent Number: 5,231,221

[45] Date of Patent: Jul. 27, 1993

[54] PROCESS FOR THE PREPARATION OF ACYLALS

[75] Inventors: Winfried Hertzsch; Gerhard Jähne, both of Frankfurt am Main, Fed. Rep. of Germany

[73] Assignee: Hoechst Aktiengesellschaft, Frankfurt am Main, Fed. Rep. of Germany

[21] Appl. No.: 671,103

[22] Filed: Mar. 18, 1991

[30] Foreign Application Priority Data

Mar. 20, 1990 [DE] Fed. Rep. of Germany ....... 4008856

[51] Int. Cl.$^5$ .................. C07C 69/003; C07C 69/017; C07C 69/62
[52] U.S. Cl. .................................... 560/263; 560/107; 560/104; 560/106; 560/112; 560/227; 560/231; 560/254; 560/261; 560/265; 560/266; 564/201; 564/208; 564/503; 568/56; 568/57
[58] Field of Search .................... 564/201, 208, 503; 568/56, 57; 560/104, 107, 106, 112, 113, 227, 231, 254, 261, 263, 265, 266

[56] References Cited

U.S. PATENT DOCUMENTS 3,165,532  1/1965  Farrissey, Jr. ...................... 562/254

FOREIGN PATENT DOCUMENTS 830850  3/1960  United Kingdom.

OTHER PUBLICATIONS

Chemical Abstracts, vol. III, No. 7, Aug. 14, 1989. O. Antonsen et al., Synthesis of sulfinylmethyl ethers and conversion of these into limlomethyl and acyloxymethyl ethers. 111:57186e.
Chung K. Chu et al. "Chemistry and Antiviral Activities of Acyclonucleosides", J. Heterocyclic Chem., 23 260–319 (1986).
J. W. Farren et al., Choroethers II, J. Am. Chem. Soc., 47 2419–2423, (1925).
E. Levas, Comptes Rendus Hebdomaires des Seanaes de l'Academie des Sciences, Paris, 228, 1443–1444 (1949).

Primary Examiner—Robert T. Bond
Attorney, Agent, or Firm—Finnegan, Henderson, Farabow, Garrett & Dunner

[57] ABSTRACT

Compounds of the formula $$R^4-\overset{O}{\underset{\|}{C}}-O-CH_2-O-\overset{R^1}{\underset{R^3}{\overset{|}{C}}}-R^2 \quad \text{I}$$

can advantageously be prepared by reacting compounds the formula II $$H-O-\overset{R^1}{\underset{R^3}{\overset{|}{C}}}-R^2 \quad \text{II}$$

in which the substituents $R^1$–$R^4$ have the meanings given, with the anhydride of the formula III $$R^4-\overset{O}{\underset{\|}{C}}-O-\overset{O}{\underset{\|}{C}}-R^4 \quad \text{III}$$

in the presence of dimethyl sulfoxide and the acid corresponding to the anhydride of the formula III.

4 Claims, No Drawings

PROCESS FOR THE PREPARATION OF ACYLALS

The present invention relates to a process for the preparation of acyloxymethoxyalkyl compounds and acyloxymethoxyphenyl compounds (acylals)

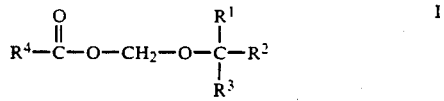

Acetoxymethoxy compounds of 2-substituted ethanediols and of 1,3-disubstituted and 2,3-disubstituted 1,2,3-propanetriols are important intermediate products because of the good acetoxy leaving group.

The acylals obtainable according to the invention are reactive compounds which are useful intermediate products, for example, in the synthesis of acyclic nucleosides (cf., for example, C. K. Chu, S. Cutler, J. Heterocyclic Chem., 23, 289 et seq. (1986)).

A method which has been known for a long time for the preparation of acylals, i.e. of esters of hemi-acetals, comprises reacting equimolar amounts of an acetal with an organic acid anhydride at elevated temperature, preferably in the presence of an acid catalyst (cf., for example, Houben-Weyl, Methoden der organischen Chemie (Methods of Organic Chemistry), Georg Thieme Verlag, Stuttgart, 1965, Volume VI/3, page 286 et seq.).

Another method uses the reaction of alpha-halogenoethers with alkali metal salts of carboxylic acids (cf., for example, J. W. Farren, J. Am. Chem. Soc. 47, 2422 (1925)). A third method utilizes the high reactivity of vinyl ethers and effects the synthesis of acylals by addition of organic acids onto vinyl ethers (see E. Levas, Comptes Rendues Hebdomadaires des Séances de 1,Academie des Sciences, Paris, 228, 1443 (1949)).

Finally, a recently published method describes the reaction of sulfinyl-methyl ethers with anhydrides of organic acids to give acylals under catalysis by methane-sulfonic acid (see O. Antonsen, T. Benneche, K. Undheim, Acta Chem. Scand. B42, 515 et seq. (1988)).

The present invention relates to a considerably simplified process for the preparation of compounds of the formula I. The advantage of the method according to the invention over that of the prior art is that the alcohol component of the acylal can be employed directly, i.e. without prior isolation of an activated intermediate product.

The invention accordingly relates to a process for the preparation of compounds of the formula I

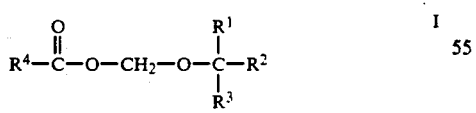

in which
$R^1$ and/or $R^2$ and/or $R^3$ are hydrogen, phenyl or alkyl which is optionally substituted by one or more alkoxy, alkenyloxy, alkylthio, alkylamino, dialkylamino, benzyloxy, benzylthio, benzylamino, dibenzylamino, acyloxy, acylthio, acylamino, diacylamino and/or phthalimido groups and/or by —P(O)(OR$^5$)(OR$^6$), —P(R$^5$)(O)(OR$^6$), —O—CH$_2$—P(O)(OR$^5$)(OR$^6$) or —O—CH$_2$—P(R$^5$)(O)-(OR$^6$) radicals, in which R$^5$ and R$^6$ in each case independently of one another can be alkyl, and $R^4$ is hydrogen, alkyl, trifluoromethyl or phenyl, or
$R^1$ is hydrogen and
$R^2$ and $R^3$ are part of a branched or unbranched carbocyclic radical, it being possible for the carbocyclic radical to contain one or more hydroxyl, mercapto, amino or alkylamino groups which are blocked by alkyl and/or acyl and/or benzyl groups, and
$R^4$ is as defined above, or
$R^4$ is an additional bond between the tertiary carbon atom and R$^2$ or R$^3$ and
$R^2$ and $R^3$ are part of a phenyl ring which can also be further substituted by alkyl groups and/or hydroxyl, mercapto, amino or alkylamino groups which are blocked by acyl and/or benzyl and/or alkyl groups, and
$R^4$ is as defined above, which comprises reacting a compound of the formula

with a compound of the formula III

in the presence of dimethyl sulfoxide and the organic acid of which the anhydride of the formula III is used, in which the radicals $R^1$-$R^4$ have the abovementioned meanings.

The process is particularly suitable for the preparation of compounds of the formula I in which
$R^1$ and/or $R^2$ and/or $R^3$ are hydrogen, phenyl, or $C_1$-$C_{12}$-alkyl which is optionally substituted by up to three $C_1$-$C_6$-alkoxy, $C_1$-$C_6$-alkylthio, $C_1$-$C_6$-alkylamino, $C_1$-$C_{12}$-dialkylamino, benzyloxy, benzylthio, benzylamino, dibenzylamino, $C_1$-$C_8$-alcyloxy, $C_1$-$C_8$-acylthio, $C_1$-$C_8$-acylamino and-/or $C_2$-$C_{16}$-diacylamino groups, it being possible for the acyl groups to be aliphatic—for example acetoxy or pivaloyloxy—or aromatic—for example benzoyloxy, and/or by —P(O)(OR$^5$)(OR$^6$), —P(R$^5$)(O)(OR$^6$), —O—CH$_2$—P(O)(OR$^5$)(OR$^6$) or —CH$_2$—P(R$^5$)(O)(OR$^6$) radicals, in which R$^5$ and R$^6$ in each case independently of one another can be $C_1$-$C_6$-alkyl, and
$R^4$ is hydrogen, alkyl, trifluoromethyl or phenyl, or
$R^1$ is hydrogen and
$R^2$ and $R^3$ are part of a branched or unbranched carbocyclic radical having 2 to 8 carbon atoms, preferably 3 to 5 carbon atoms in the carbocyclic part, it being possible for the carbocyclic radicals to contain one or more hydroxyl, mercapto, amino or $C_1$-$C_6$-alkylamino groups which are blocked by $C_1$-$C_6$-alkyl and/or $C_1$-$C_8$-acyl and/or benzyl groups, and
$R^4$ is as defined above, or
$R^1$ is an additional bond between the tertiary carbon atom and R$^2$ or R$^3$ and
$R^2$ and $R^3$ are part of a phenyl ring which can also be further substituted by $C_1$-$C_4$-alkyl groups and/or hydroxyl, mercapto, amino or $C_1$-$C_4$-alkylamino groups which are blocked by $C_1$-$C_8$-acyl and/or benzyl and/or $C_1$-$C_6$-alkyl groups, and $R^4$ is as defined above.

The process is particularly preferred for the preparation of compounds of the formula I in which $R^1$ and $R^2$ are hydrogen and $R^3$ is $C_1$-$C_{12}$-alkyl, or $R^1$ is hydrogen and $R^2$ and $R^3$ are $C_1$-$C_{12}$-alkyl, it being possible for this $C_1$-$C_{12}$-alkyl to be substituted by up to two $C_1$-$C_6$-alkoxy, $C_1$-$C_6$-alkylthio, benzyloxy, benzylthio, dibenzylamino, $C_1$-$C_8$-acyloxy, $C_1$-$C_8$-acylthio and/or $C_2$-$C_{16}$-diacylamino groups—it being possible for the acyl groups to be aliphatic—for example acetoxy or pivaloyloxy—or aromatic—for example benzoyloxy—and/or by $-P(O)(OR^5)(OR^6)$, $-P(R^5)(O)(OR^6)$, $-O-CH_2-P-(O)(OR^5)(OR^6)$ or $-O-CH_2-P-(R^5)(O)(OR^6)$ radicals, in which $R^5$ and $R^6$ in each case independently of one another are $C_1$-$C_6$-alkyl, and $R^4$ is alkyl, trifluoromethyl or phenyl.

The abovementioned process is particularly suitable for the preparation of the abovementioned compounds in which $R^4$ is $C_1$-$C_6$-alkyl, in particular $C_1$-$C_3$-alkyl.

The process according to the invention is of special importance for the reaction of acetic anhydride as the compound of the formula III (i.e. $R = CH_3$).

If the radicals $R^1$ and/or $R^2$ and/or $R^3$ of the abovementioned compounds carry acyl groups, uniform products are obtained in particular if these acyl groups are identical to the $R^4-C(O)$ group in formula III.

The alkyl groups mentioned as substituents can be straight-chain, branched or cyclic.

The acyl groups mentioned can be straight-chain, branched, cycloaliphatic or aromatic.

The compounds of the formula I can contain one or more chiral centers. The compounds are as a rule present as racemates; it is possible to prepare and isolate the pure enantiomers. The invention therefore relates both to the process for the preparation of the pure enantiomers and to mixtures thereof, such as, for example, the associated racemate.

The alkyl, acyl or benzyl protective groups with which hydroxyl, mercapto or amino groups of the substituents $R^1$ to $R^3$ are blocked if appropriate, can be split off by customary methods, such as, for example, by reaction with boron halides, hydrolysis or hydrogenolysis.

For carrying out the process according to the invention, an alkanol of the formula II, an anhydride of the formula III, the carboxylic acid corresponding to the anhydride and dry dimethyl sulfoxide are preferably brought together at a temperature of $-10°$ to $40°$ C., particularly preferably $0°$ to $30°$ C., while stirring. The molar ratio of anhydride:carboxylic acid:dimethyl sulfoxide to 1 mol of alkanol is preferably 2-10:1.5-20:1-30, particularly preferably 4-6:6-14:10-20, and in particular about 5:about 10:about 15. The reaction mixture is preferably stirred for 1-24 hours, particularly preferably 5-7 hours, at $0°$-$100°$ C., in particular at $30°$-$90°$ C.

The reaction mixture can be worked up by conventional methods.

The working up is preferably carried out, for example, by pouring the resulting reaction mixture into ice-water and extracting it by shaking three times with an ether, preferably diethyl ether or diisopropyl ether. The organic phase is then extracted by shaking 3 times with water and then several times with concentrated sodium bicarbonate solution, until the aqueous wash water no longer has an acid reaction. The mixture is then extracted by shaking with water once again and the organic phase is dried over sodium sulfate, filtered and freed from the solvent under reduced pressure. The residue is subjected, for example, to fractional distillation and gives, in addition to the acyloxymethyl thiomethyl ether, the acyloxymethyl compound of the alkanol employed. The present invention is illustrated in more detail by the following embodiment example.

Example

Compound of the formula I in which $R1$ = hydrogen, $R2$ = $R3$ = isopropoxymethyl, $R4$ = methyl:

200 ml of dry dimethyl sulfoxide are added dropwise to a mixture of 120 ml of glacial acetic acid and 100 ml of acetic anhydride, while stirring, so that the temperature of the mixture does not rise above 35 degrees Celsius. The mixture is stirred for a further 30 minutes before 35.2 g (0.2 mol) of 1,3-bis-isopropoxy-propan-2-ol (prepared by reaction of sodium isopropylate with 2,3-epoxypropyl isopropyl ether in isopropanol) are added dropwise. When the addition has ended, the mixture is heated at 90-100 degrees Celsius for 7 hours. The cooled reaction mixture is poured into ice-water and extracted by shaking several times with diethyl ether. The organic phase is then washed with water and subsequently with concentrated aqueous sodium bicarbonate solution, dried over sodium sulfate and concentrated under reduced pressure. A pale yellow oil remains and is subjected to fractional distillation. First runnings of boiling point 46-47 degrees Celsius under a pressure of 15 mm Hg comprise acetoxymethyl thiomethyl ether. The reaction product, 2-acetoxymethoxy-1,3-bis-isopropoxypropane, boils at 87-92 degrees Celsius under a pressure of 1 mm Hg. The yield is 27.3 g (55% of theory). 1H-NMR (60 MHz, $CDCl_3$), $\delta$ [ppm]: 5.43 (s, 2H), 4.0-3.33 (m, 7H), 2.12 (s, 3H), 1.33 (d, 12H).

The following compounds can be prepared in a similar manner:

1-acetoxymethoxy-2-methoxy-ethane
1-acetoxymethoxy-2-ethoxy-ethane
1-acetoxymethoxy-2-propoxy-ethane
1-acetoxymethoxy-2-isopropoxy-ethane
1-trifluoroacetoxymethoxy-2-isopropoxy-ethane
1-benzoyloxymethoxy-2-isopropoxy-ethane
1-acetoxymethoxy-2-butoxy-ethane
1-acetoxymethoxy-2-benzyloxy-ethane
1-acetoxymethoxy-2-phenoxy-ethane
1-acetoxymethoxy-2-acetoxy-ethane
1-acetoxymethoxy-2-pivaloyloxy-ethane
2-acetoxymethoxy-3-methoxy-propane
di-isopropyl (2-acetoxymethoxy-ethoxy)methane-phosphonate isopropyl ((2-acetoxymethoxy-ethoxy)methyl)-methylphosphinate
di-isopropyl (3-acetoxymethoxy)propane-phosphonate
1-acetoxy-methoxy-2-benzyloxy-3-isopropoxy-propane
1-benzoyloxymethoxy-2-benzyloxy-3-isopropoxy-propane
1-acetoxymethoxy-2-benzyloxy-3-methoxy-propane
1-acetoxtmethoxy-2-benzyloxy-3-ethoxy-propane
1-acetoxymethoxy-2,3-bis-benzyloxy-propane
1-acetoxymethoxy-2,3-bis-(isopropoxy)-propane
1-acetoxymethoxy-2-benzyloxy-3-(N-phthalimido)-propane
1-acetoxymethoxy-2-benzyloxy-3-methylthio-propane
1-acetoxymethoxy-2-benzyloxy-3-ethylthio-propane
di-isopropyl (4-acetoxymethoxy-3-benzyloxy)butane-phosphonate
2-acetoxymethoxy-1,3-bis(methoxy)-propane
2-acetoxymethoxy-1,3-bis(ethoxy)-propane 2-acetoxymethoxy-1,3-bis(propoxy)-propane
2-acetoxymethoxy-1,3-bis(isopropoxy)-propane
2-trifluoroacetoxymethoxy-1,3-bis(isopropoxy)-propane
2-benzoyloxymethoxy-1,3-bis(isopropoxy)-propane
2-acetoxymethoxy-1,3-bis(prop-2-en-1-oxy)-propane
2-acetoxymethoxy-1,3-bis(benzyloxy)-propane
2-acetoxymethoxy-1-isopropoxy-3-(1,1,2,2-tetrafluoroethoxy)-propane
di-isopropyl (3-acetoxymethoxy-4-benzyloxy)butanephosphonate
2-acetoxymethoxy-1,3-bis(cyclopentyloxy)-propane
2-acetoxymethoxy-1,3-bis(cyclohexyloxy)-propane
2-acetoxymethoxy-1-benzyloxy-3-isopropoxy-propane
2-acetoxymethoxy-1-benzyloxy-3-methoxy-propane
2-acetoxymethoxy-1-isopropoxy-3-methoxy-propane
2-acetoxymethoxy-1-isopropoxy-3-[1,3-bis(isopropoxy)-2-propoxy]-propane
2-acetoxymethoxy-1-isopropoxy-3-pivaloyloxy-propane
2-acetoxymethoxy-1-benzyloxy-3-pivaloyloxy-propane
2-acetoxymethoxy-1,3-bis(pivaloyloxy)-propane
2-acetoxymethoxy-1-isopropoxy-3-phenoxy-propane
2acetoxymethoxy-1-isopropoxy-3-(N-phthalimido)-propane acetoxymethoxy-cyclohexane acetoxymethoxy-benzene.

The corresponding propanoyloxymethoxy, butanoyloxymethoxy or isobutanoyloxymethoxy compounds can be obtained in a similar manner using propionic acid and propionic anhydride, or butyric acid and butyric anhydride, or iso-butyric acid and isobutyric anhydride.

What is claimed is:

1. A process for the preparation of a compound of the formula

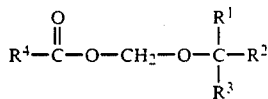

in which
R$^1$ and/or R$^2$ and/or R$^3$ are hydrogen, phenyl, C$_1$-C$_{12}$-alkyl or C$_1$-C$_{12}$-alkyl which is substituted by one or more C$_1$-C$_6$-alkoxy, C$_1$-C$_6$-alkenyloxy, C$_1$-C$_6$-alkylthio, C$_1$-C$_{12}$-alkylamino, C$_1$-C$_6$-dialkylamino, benzyloxy, benzylthio, benzylamino, dibenzylamino, C$_1$-C$_8$-acyloxy, C$_1$-C$_8$-acylthio, C$_1$-C$_8$-acylamino and/or C$_2$-C$_{16}$-diacylamino groups wherein the acyl groups are acetoxy, pivaloyloxy or benzoyloxy, and
R$^4$ is hydrogen, C$_1$-C$_6$-alkyl, trifluoromethyl or phenyl, which comprises reacting a compound of the formula II

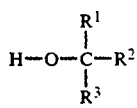

with a compound of the formula III

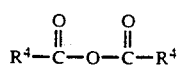

in the presence of dimethyl sulfoxide and the organic acid of which the anhydride of the formula III is used, in which the radicals R$^1$-R$^4$ have the above meanings.

2. The process as claimed in claim 1, wherein the molar ratio of the reactants anhydride of the formula III/carboxylic acid/dimethyl sulfoxide to be employed per mol of alkanol of the formula II is 2-10/1.5-20/1-30.

3. The process as claimed in claim 1, wherein the reactants are brought together at a temperature of −10°-30° C., while stirring, and the resulting reaction mixture is stirred at a temperature of 0° to 100° C. for 1 to 24 hours.

4. A process for the preparation of a compound of the formula I

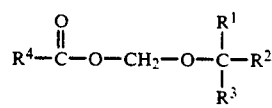

in which
R$^1$ and/or R$^2$ and/or R$^3$ are hydrogen, phenyl, C$_1$-C$_{12}$-alkyl or C$_1$-C$_{12}$-alkyl which is substituted by one or more C$_1$-C$_6$-alkyloxy, C$_1$-C$_6$-alkenyloxy, C$_1$-C$_6$-alkylthio, C$_1$-C$_6$-alkylamino, C$_1$-C$_{12}$-dialkylamino, benzyloxy, benzylthio, benzylamino, dibenzylamino, C$_1$-C$_8$-acyloxy, C$_1$-C$_8$-acylthio, C$_1$-C$_8$-acylamino and/or C$_2$-C$_{16}$-diacylamino groups wherein the acyl groups are acetoxy, pivaloyloxy or benzoyloxy, and
R$^4$ is hydrogen, C$_1$-C$_6$-alkyl, trifluoromethyl or phenyl, which comprises reacting a compound of the formula II

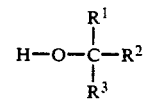

with a compound of the formula III

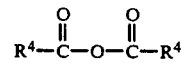

in the presence of dimethyl sulfoxide and the organic acid of which the anhydride of the formula III is used, in which the radicals R$^1$-R$^4$ have the above meanings, wherein the molar ratio of the reactants anhydride of the formula III/carboxylic acid/dimethyl sulfoxide to be employed per mol of alkanol of the formula II is 2-10/1.5-20/1-30, and wherein the reactants are brought together at a temperature of −10°-30° C., while stirring, and the resulting reaction mixture is stirred at a temperature of 0° to 100° C. for 1 to 24 hours.

* * * * *